Figure 1:
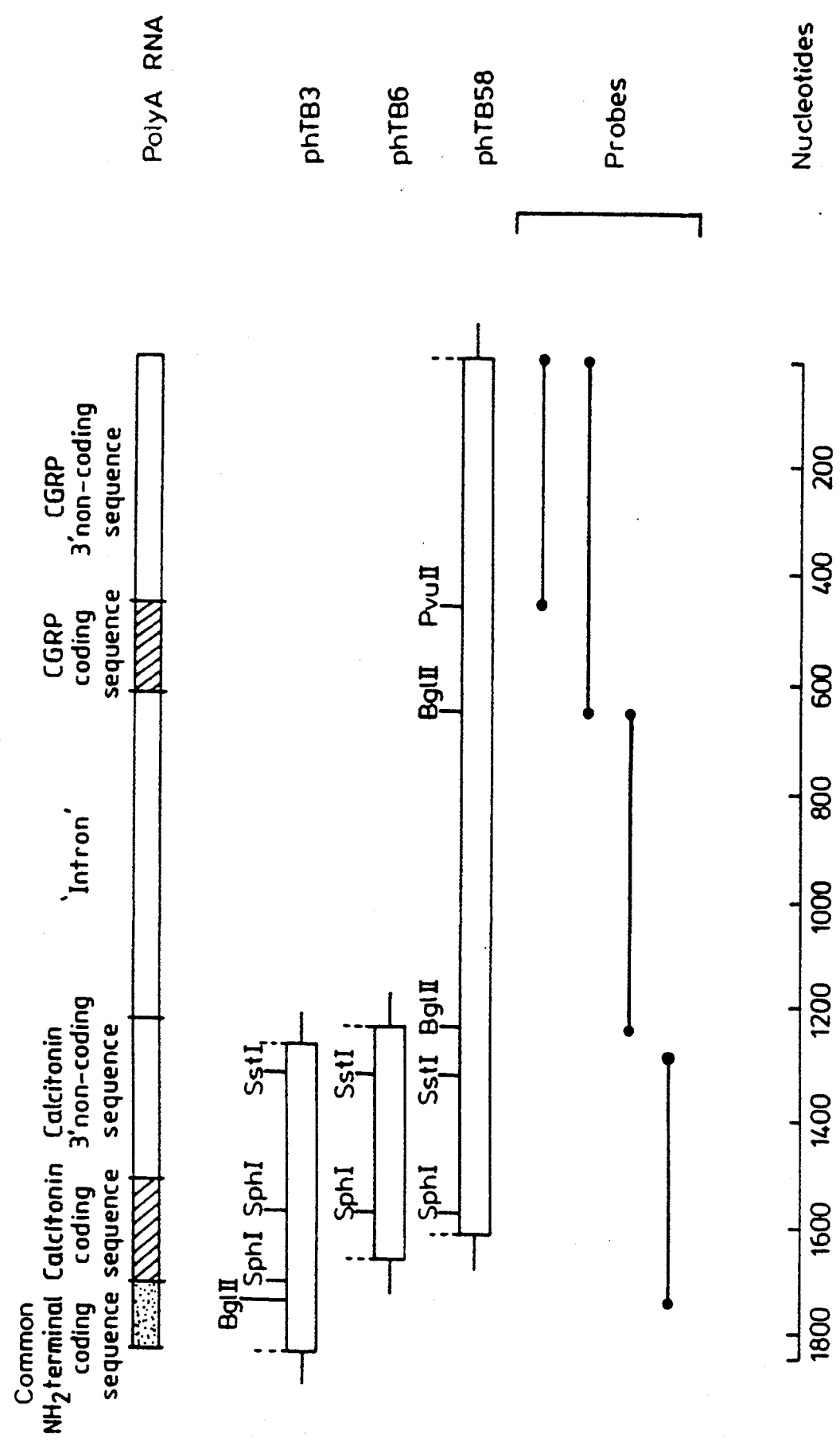

United States Patent [19]
Craig et al.

[11] Patent Number: 5,374,618
[45] Date of Patent: Dec. 20, 1994

[54] CALCITONIN PEPTIDES, AND GENE RELATED PHARMACEUTICAL COMPOSITIONS

[75] Inventors: Roger K. Craig; Mark R. Edbrooke, both of London, England

[73] Assignee: Celltech Limited, Slough, Great Britain

[21] Appl. No.: 705,423

[22] PCT Filed: Jun. 15, 1984

[86] PCT No.: PCT/GB84/00210
§ 371 Date: Feb. 14, 1985
§ 102(e) Date: Feb. 14, 1985

[87] PCT Pub. No.: WO85/00043
PCT Pub. Date: Jan. 3, 1985

[30] Foreign Application Priority Data

Jun. 15, 1983 [GB] United Kingdom ................. 8316296
Nov. 1, 1983 [GB] United Kingdom ................. 8329093

[51] Int. Cl.$^5$ ..................... A61K 37/02; C07K 7/10
[52] U.S. Cl. ..................... 514/12; 530/307; 530/324
[58] Field of Search ................. 514/12; 530/324, 307

[56] References Cited

FOREIGN PATENT DOCUMENTS 0070186 1/1983 European Pat. Off. .
0070675 1/1983 European Pat. Off. .
8304028 11/1983 WIPO .

OTHER PUBLICATIONS

Chemical Abstracts vol. 93, 1980 Pt. 218.
"Isolation and Characterization of Human Calcitonin Gene-related Peptide" by H. R. Morris et al, *Nature*, vol. 308, Apr. 19, 1984, pp. 746–748.
"Calcitonin mRNA Polymorphism: Peptide Switching Associated With Alternative RNA Splicing Events", by M. G. Rosenfeld et al, *Proc. Natl. Acad. Sci. USA* vol. 79, pp. 1717 to 1721, Mar. 1982, Biochemistry.
"The Construction and Partial Characterization of Plasmids Containing Complementary DNA Sequences to Human Calcitonin Precursor Polyprotein", by N. Allison et al, *Biochem. J.* (1981) 199, pp. 725–731.
"Partial Nucleotide Sequence of Human Calcitonin Precursor mRNA Identifies Flanking Cryptic Peptides", by Roger K. Criag et al, *Nature*, vol. 295, 28 Jan. 1982, pp. 345 to 347.
"Alternative RNA Processing in Calcitonin Gene Expression Generates mRNAs Encoding Different Polypeptide Products", by Susan G. Amara et al, *Nature*, vol. 298, 15 Jul. 1982, pp. 240–244.

*Primary Examiner*—Lester L. Lee
*Attorney, Agent, or Firm*—Cushman, Darby & Cushman

[57] ABSTRACT

This invention relates to human gene related peptide pharmaceutical compositions containing the peptide and the method of treating hypertension with said pharmaceutical composition.

4 Claims, 16 Drawing Sheets

FIG. 2A

```
      -36  -35  -34  -33  -32  -31  -30  -29  -28  -27  -26  -25
      Val  Leu  Leu  Ala  Ala  Leu  Val  Gln  Asp  Tyr  Val  Gln
 1836                                                         1800
5'    GTC  CTG  CTG  GCT  GCA  CTG  GTG  CAG  GAC  TAT  GTG  CAG
      CG        A                             A         A
      Arg                                     Asn       Met

-24  -23  -22  -21  -20  -19            -18  -17  -16  -15
      Met  Lys  Ala  Ser  Glu  Leu            Glu  Gln  Glu  Gln

ATG  AAG  GCC  AGT  GAG  CTG_____GAG  CAG  GAG  CAA
                A    T                GAG  CAG       G    A    G
                     Val  Arg         Glu  Gln            Glu

-14  -13  -12  -11  -10
      Glu  Arg  Glu  Gly  Ser

GAG  AGA  GAG  GGC  TCC
                GCT            T
                Ala
```

```
       -9   -8   -7   -6   -5   -4   -3 │ -2   -1 │  1    2    3    4
       Ser  Leu  Asp  Ser  Pro  Arg  Ser│ Lys  Arg│ Cys  Gly  Asn  Leu
            1750                        │         │
       AGC  CTG  GAC  AGC  CCC  AGA  TCT│ AAG  CGG│ TGC  GGT  AAT  CTG
       ▲    T                           │         │      T    G
       A                                │         │

5    6    7    8    9   10   11   12   13   14   15   16   17
       Ser  Thr  Cys  Met  Leu  Gly  Thr  Tyr  Thr  Gln  Asp  Phe  Asn
                                1700
       AGT  ACT  TGC  ATG  CTG  GGC  ACA  TAC  ACG  CAG  GAC  TTC  AAC
            C                             G         A    A         C
                                                                   Leu 18   19   20   21
       Lys  Phe  His  Thr

AAG  TTT  CAC │ ACG
                     │ C
                     └─────→phTB6
```

FIG. 2B

```
 22   23   24   25   26   27   28   29   30   31   32  | +1   +2
Phe  Pro  Gln  Thr  Ala  Ile  Gly  Val  Gly  Ala  Pro  | Gly  Lys
                    1650
TTC  CCC  CAA  ACT  GCA  ATT  GGG  GTT  GGA  GCA  CCT | GGA  AAG
                    T                                 |   C
                    Ser

+3   +4 | +5   +6   +7   +8   +9  +10  +11  +12  +13  +14  +15
Lys  Arg| Asp  Met  Ser  Ser  Asp  Leu  Glu  Arg  Asp  His  Arg
        |                           1600
AAA  AGG| GAT  ATG  TCC  AGC  GAC  TTG  GAG  AGA  GAC  CAT  CGC
        |           G    AG                    C    A    C    A
        |           Ala  Lys                   Thr  Asn       His
        |
        └──> phTB58

+16  +17  +18  +19
Pro  His  Val  Ser

CCT  CAT  GTT  AGC
 C    T    T    G
      Tyr  Phe  Gly

+20  +21  +22  +23  +24  +25
Met  Pro  Gln  Asn  Ala  Asn  term
                              1550
ATG  CCC  CAG  AAT  GCC  AAC  TAA  ACTCCTCCCTTTCCTTCCTAATT
--------------------------     G   GTC     TC C T     -- G 1500
       TCCCTTCTTGCATCCTTCCTATAACTTGATGCATGTGGTTTGGTTCCTCTC
        T T                                A    -----

TGGTGGCTCTTTGGGCT
   CT T    C
```

FIG. 2C

```
                    1450
GGTATTGGTGGCTTTCCTTGTGGCAGAGGATG___TCTCAAACTTCAGATG
AT    G  TA       A - A    A       GTA  GG  TC  CA

1400
GGAGGAAAGAGAGCAGGACTCACAGGTTGGAAGAGAATCACCTGGGAAAAT
   T  AGG    A    G

1350
ACCAGAAAATGAGGGCC

1300
GCTTTGAGTCCCCCAGAGATGTCATCAGAGCTCCTCTGTCCTGCTTCTGAA
                                                phT

TGTGCTGATCATTTGAGGAATAAAATTATTTTTCCCCAAAGATCTGAGCTG

B3 <──┘

TGGTGGTCATTGCTCTG

1200
ATCTATGTCCCAGGCTTCATAGTGTCTAAGACCTATGCTTAGAAATAGCCT

1150
TAACCCTAGGCTAGCTGGACAGAGGATATGGTGGGTGGTCCCTTTGACCAA

GCTCAAGCAGGAAGAAC

1100
AGGGGTCCTAAGGAGCAGGTAAGCACCTCTAGGACTTGATGCTGCAAACTC

1050
GCTCCTCTTCCAGGTAAGACTGAGGAATTTTTTATTTTCCTAAGAAAGGGT

1000
ATTTGGTGCCCGTGAC
```

FIG. 2D

```
                                              950
TGGGGTGTAGATTTTATAGTCCTTTGTGAATGGGGCTGGGTGTGGGACCAT

900
AATTCACTCCAGTGTCATAAACCTCCGCTTTGATTTTTAGTTAATTTATAC

AGGAAAGATTGGCTGTT

850
ACTGCTCCACATTCCATAGCCAGTCATCCAGAGTCACCTTGGGTTTCTGAC

800
ACCCCTGGGAATATCTATGGGGAGTGATCATGGCATTTTCCCTAATGGCCT

TGTGATTTTCTGCTCTG 750                                                700
ATAATTGTGTTTAGGAGAAACACTTAAAGTTAATTGGTGCCTTTCAGCACA

650
GCAACTTTACCATGAAGGTCCCATGGGGCTGACCTCTCTCCCAGCCTCTCA

CTCACAGATCTTCTCTT
```

```
                        -7  -6  -5  -4  -3 │-2  -1
                        Arg Ile Ile Ala Gln│Lys Arg
                                        600
CTTTCTCCATCCTGCAAATCAG  A   ATC ATT GCC CAG│AAG AGA
                        A T     G   C
                            T
                        Ser Val Thr
                            Val Thr
```

```
1    2    3    4    5    6    7    8    9    10   11   12   13
Ala  Cys  Asp  Thr  Ala  Thr  Cys  Val  Thr  His  Arg  Leu  Ala

GCC  TGT  GAC  ACT  GCC  ACC  TGT  GTG  ACT  CAT  CGG  CTG  GCA
T         C    A                                C    C
Ser            Asn 14   15   16   17
Gly  Leu  Leu  Ser
 550
GGC  TTG  CTG  AGC
```

FIG. 2E

```
 18  19  20  21  22  23  24  25  26  27  28  29  30
Arg Ser Gly Gly Val Val Lys Asn Asn Phe Val Pro Thr

AGA TCA GGG GGT GTG GTG AAG AAC AAC TTT GTG CCC ACC
 G   G   A                   G
                            Asp 31  32  33  34  35  36  37 | +1  +2  +3  +4  +5 | +6
Asn Val Gly Ser Lys Ala Phe | Gly Arg Arg Arg Arg| Asp
500
AAT GTG GGT TCC AAA GCC TTT | GGC AGC CGC CGC AGG| GAC
         C   T   G       C  |     C C
                Glu

+7  +8  +9
Leu Gln Ala term

CTT CAA GCC TGA
     G   T
```

```
450
 GCAGCTGAATGACTC___AAGAAGGT__CACAATAAAGCTGAACTC_____
 A      A A TA C C AGA    ▲ TA          A A      TAATT
                          B
        400
 CTTTTAATGTGTAATGAAAGCAATTTGTAGGAAAGGCTCCATGGAAGACAT
         C    A    T    TC G   CA         GA

350
 ACATATAGGCATCCT
```

FIG. 2F

```
                                                    300
TCTTGATACTGAAAACAATCTTCTTGTTTGAAAGGAACTATTGCTAAATGC

250
AGAACAAGCTCATTGCAGTTACCTATTGTGCATCTTTTTAAATACTTGATT

ATGTAACCATAAATCTG

200
ACAGCATGTCTCATTGGCTTATCTGGTAGCAAATCTAGGCCCCGTCAGCCA

150
CCCTATTGACATTGGTGGCTCTGCTTAAACCTCAGGGGACATGAAATCAC

TGCCTCTTGGGCATCTGG

100
GGACACATGGTAATGCTGTGCCTTGACAGAAGTATTTGTTTAAAGAAATGTC

50
AATGCTGTCATTTGTGAACTCTATCAAAATTAAAAATGTATTTTATCTACCC

TT poly A 3'
```

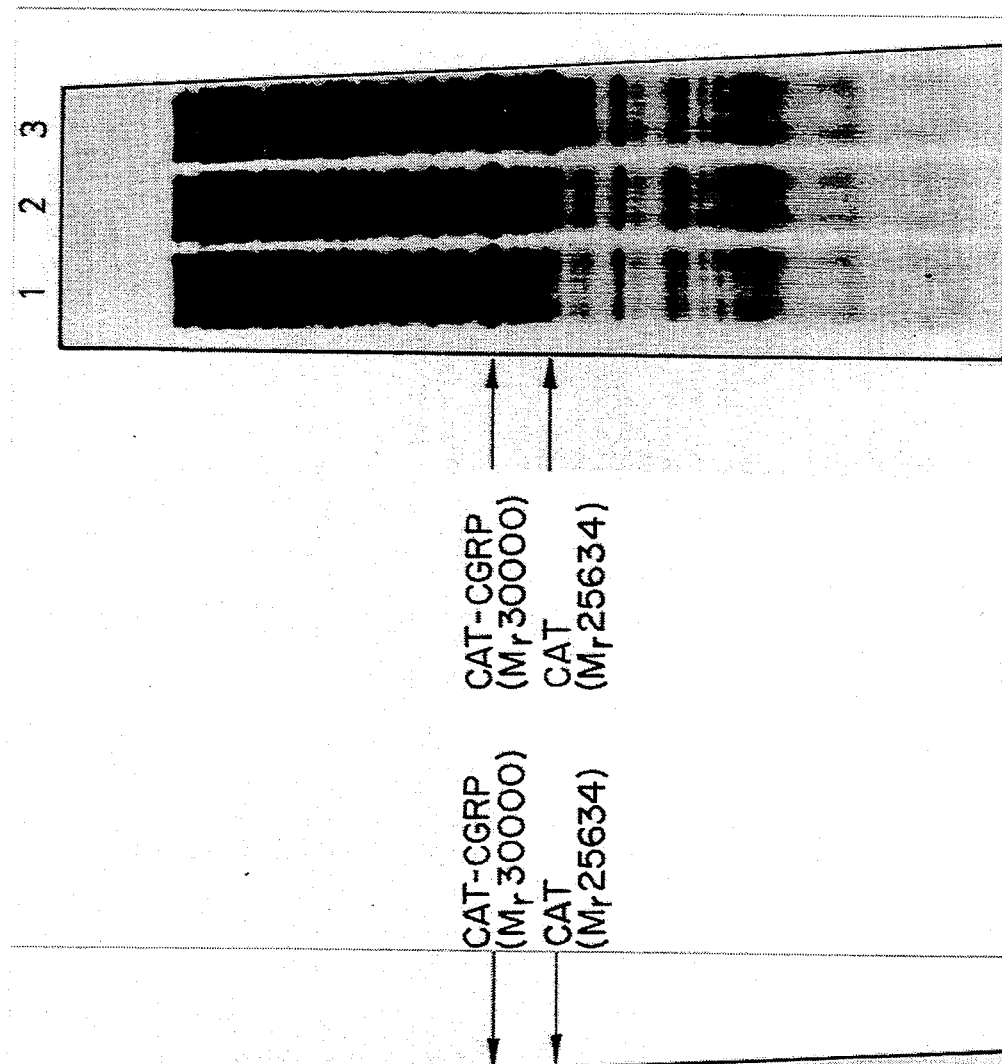
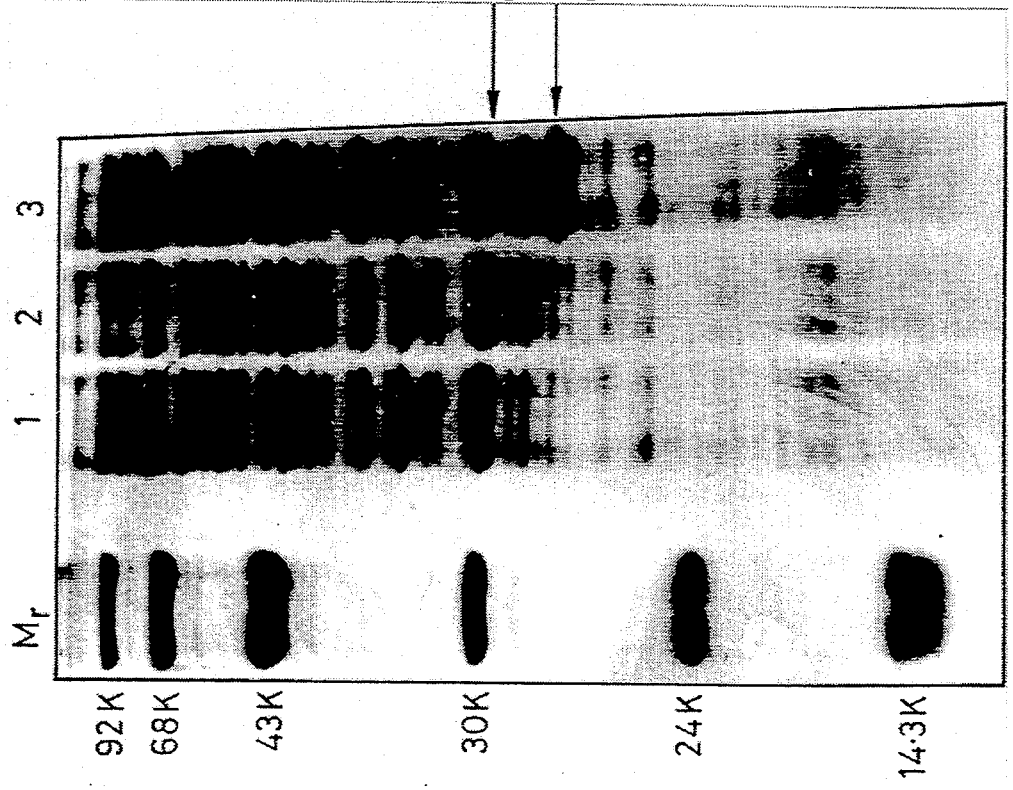

CALCITONIN PEPTIDES, AND GENE RELATED PHARMACEUTICAL COMPOSITIONS

FIELD OF THE INVENTION

This invention relates to peptides, pharmaceutical compositions, processes for producing the peptides, genes coding for the peptides, vectors including the genes and host organisms transformed with the vectors, and gene probes and antibodies for use in diagnosis.

BACKGROUND OF THE INVENTION

The calcitonin gene system has been the subject of considerable research in recent years. In particular, studies on rat calcitonin gene expression have demonstrated the generation, by RNA processing, of alternative mRNA species in an apparently tissue specific manner to produce different peptide hormones from a single gene. (Craig R. K. et al (1983) Genetic Engineering 4, 57–125 and Amara et al (1982) Nature 298, 240–244). Each mRNA species encodes a polyprotein cleaved by post translational processing events to yield either rat calcitonin or rat calcitonin gene related peptide (rat CGRP). The rat CGRP is known to be widely distributed in discrete regions of the central and peripheral nervous system where it has been shown to have potent biological activity (Fisher et al (1983) Nature, 305, p 534–536).

In copending European patent applications EP-A1-0070186 and EP-A1-0070675 (R. K. Craig and I. MacIntyre) there are described the production of human calcitonin and a carboxy terminal peptide designated PDN-21 (Katacalcin). Human calcitonin and katacalcin are formed as a polyprotein encoded by the human calcitonin mRNA (Craig et al (1982) Nature, 295, p 345–347).

We have now discovered a region of the human calcitonin gene which is transcribed in human medullary carcinoma cells, and is located distal to the 3′ translated region of the human calcitonin mRNA. The region comprises a transcribed intron region, a splice junction, an open reading frame which encodes previously unknown human peptide sequences, and a 3′ untranslated region terminating with a tract of poly A residues. One of the peptides is apparently an analogue of rat CGRP, which analogue we refer to hereinafter as human calcitonin gene related peptide (human CGRP).

SUMMARY OF THE INVENTION

According to a first aspect of the invention, we provide human calcitonin gene related peptide.

According to a second aspect of the present invention we provide a peptide having the structure Ala—Cys—Asp—Thr—Ala—Thr—Cys—Val—Thr—His—Arg— (I)
—Leu—Ala—Gly—Leu—Leu—Ser—Arg—Ser—Gly—Gly—
—Val—Val—Lys—Asn—Asn—Phe—Val—Pro—Thr—Asn—
—Val—Gly—Ser—Lys—Ala—Phe—amide.

This novel peptide is formed as part of a polyprotein which is specifically cleaved in vivo within the secretory pathway by proteolytic enzymes which recognise flanking basic amino acid residues. The peptide (which has been designated PAF-37 in accordance with the terminology of Tatemoto and Mutt (1981) PNAS 78 p 6603–6607) has been found to have a potent biological effect in the modulation of cardiovascular function. In particular the peptide has been shown to induce hypotension and to increase heart beat rate and force.

In a second aspect of the invention the peptide is provided for use as a pharmaceutical, preferably for use in treatment of hypertension. It is common, in the post operative stages of major heart surgery (for example in open heart bypass operations), for the patient to react to the stress of the operation by extensive vasoconstriction. This has the effect of increasing the patient's blood pressure, thus straining the heart. The peptide of the invention has been shown to act as a hypotensive agent and to increase the force of heart beat. These combined effects make it of potential use as a post-operative treatment. A large percentage of people suffer from hypertension and it is a strong contributory factor in the high incidence of heart failure. The peptide may be used in the management of hypertension.

In a third aspect of the invention we provide a pharmaceutical composition comprising a peptide of the structure (I) and a pharmaceutically acceptable excipient. Preferably the composition is an injectable composition. The pharmaceutical composition may be contained within, or form part of, a system for the controlled slow release of the composition or the peptide in or into the body. Such a controlled slow release system is of use in the long term management of hypertension.

We further provide a method of treatment of hypertension comprising administering an effective amount of the peptide of the structure (I). We also provide a process for preparing a pharmaceutical composition according to the third aspect of the invention comprising the step of bringing a peptide of the structure (I) into association with a pharmaceutically acceptable excipient.

The peptide of structure (I) may be produced by a variety of processes.

The peptide may be produced by chemical peptide synthesis using techniques well known in the art. A number of commercial concerns now specialise in the custom synthesis of peptides. Purification of the peptide may be conducted using the techniques of ion and reverse phase chromatography.

In a fourth aspect of the invention we provide a peptide comprising at least the amino acid sequence as follows:

Ala—Cys—Asp—Thr—Ala—Thr—Cys—Val—Thr—His— (II)
—Arg—Leu—Ala—Gly—Leu—Leu—Ser—Arg—Ser—Gly—
—Gly—Val—Val—Lys—Asn—Asn—Phe—Val—Pro—
—Thr—Asn—Val—Gly—Ser—Lys—Ala—Phe—R′ wherein R′ is -H or an amino acid residue or a peptide convertible into amide in vivo or in vitro. R′ may be -Gly-, -Gly-Arg-Arg-Arg-Arg or -Gly-Lys-Lys-Arg but is preferably -Gly. The carboxy terminal residue R′ may be converted enzymically in vivo or in vitro to an amide on the adjacent phenylalanine amino acid residue. A suitable enzyme for this conversion when R′ is -Gly is yeast carboxypepdidase Y, or the mammalian amidation enzyme. (Bradbury, A. F., Finnie, M. D. A. & Smyth, D. G. (1982) Nature, 298, 686–688).

Alternatively and preferably the peptide is produced by a recombinant DNA technique.

In a fifth aspect of the invention we provide a process for the preparation of a peptide of the structure (I) comprising the steps of culturing a host organism transformed with a vector including a gene coding for an intermediate peptide wherein the intermediate peptide is a peptide according to the fourth aspect of the invention to produce the intermediate peptide and converting R' to amide.

Preferably the intermediate peptide is a fusion protein comprising at least a portion of a protein produced in a transformed host organism and the amino acid sequence defined as (II) above. Desirably the fusion proteins include a protein produced at a high level by a transformed host organism. Suitable such proteins include at least a portion of a chloramphenicol acetyltransferase (CAT) protein or at least a portion of the β-galactosidase protein. Preferably the fusion protein comprises a peptide having the amino acid sequence defined as (II) above linked to the carboxy terminus of the protein produced at high levels in a transformed host organism. Preferably the peptide is linked to the protein through a linkage capable of selective chemical or enzymic cleavage. The linkage may be a methionine or glutamic acid amino acid residue. Methionine may be selectively cleaved by cyanogen bromide and glutamic acid may be selectively cleaved by using an acid protease from Sorghum (EC 3.4.23.14), sea urchin hatching protease (EC 3.4.24.12) or, preferably, staphylococcal protease (EC 3.4.21.19). (The human CGRP sequence contains no Met or Glu residues). The linkage may be a lysine-arginine peptide diradical. Cleavage of this linkage may be achieved using a mouse sub-maxillary gland protease or, preferably, clostripain (EC 3.4.21.6).

The peptide of the first and second aspects of the invention is produced as a polyprotein in the body. The polyprotein is processed by the body to cleave amino and carboxy terminus groups leaving the amidated 37 amino acid peptide of the first or second aspect of the invention. In a sixth aspect of the invention we provide a process for the production of peptide of the structure (I) comprising the steps of culturing a eucaryotic host organism transformed with a vector including a gene coding for an intermediate peptide including at least the amino sequence Arg—Ile—Ile—Ala—Gln—Lys—Arg—Ala—Cys—Asp—    (III)
—Thr—Ala—Thr—Cys—Val—Thr—His—Arg—Leu—Ala—
—Gly—Leu—Leu—Ser—Arg—Ser—Gly—Gly—Val—Val—Lys—
—Asn—Asn—Phe—Val—Pro—Thr—Asn—Val—Gly—Ser—
—Lys—Ala—Phe—Gly—Arg—Arg—Arg—Arg—Asp—Leu—
—Gln—Ala to produce the intermediate peptide, allowing processing of the intermediate peptide by the host organism and isolating the peptide. Preferably the eucaryotic host organism is a tissue cultured mammalian cell line containing proteolytic and amidating enzymes capable of producing the peptide of structure I from a polyprotein including amino acid sequence III. Preferably the intermediate peptide is produced as a fusion protein.

In the processing of the polyprotein a tetrapeptide is produced. This tetrapeptide also has biological activity, and is also a feature of the invention, having the following sequence:

Asp-Leu-Gln-Ala    (IV)

This peptide is denoted PDA-4 and has been found to have biological effect in the modulation of cardiovascular function. In particular the peptide has been shown to induce hypotension and to increase rate of heart beat.

In an eighth aspect of the invention we provide a peptide of sequence IV for use as a pharmaceutical, preferably for use in the treatment of hypertension.

In a ninth aspect of the invention we provide a pharmaceutical composition comprising a peptide of the sequence (IV) and a pharamceutically acceptable excipient. Preferably the composition is an injectable composition. The pharmaceutical composition may be contained within, or form part of, a system for the controlled slow release of the composition or peptide in or into the body. The composition may contain a combination of the peptides of structure I and the peptide of sequence IV and a pharmaceutically acceptable excipient.

In a tenth aspect of the invention we provide a gene coding for PAF-37 (structure I), PAF-37-R' (structure II) PDA-4 (structure IV) or an 'unprocessed' peptide (structure III). Preferably we provide the specific genes defined by the nucleotides corresponding to the following amino acids the lower half of FIG. 2; i) 1 to 37 inclusive ii) −3 to −7 inclusive iii) +6 to +9 inclusive or iv) amino acids −7 to +9 inclusive. We also provide nucleotide sequence substantially as shown in FIG. 2 from nucleotides 1 to 1256 inclusive. We further provide a vector including any of these genes and a host organism transformed with such a vector. Suitable host organisms include bacteria (e.g. *E. coli*), yeasts (e.g. *Saccharomyces cerivisiae*) and mammalian cells in tissue culture.

The production of human CGRP is tissue dependent due to an alternative, tissue mediated, mRNA processing. (Edbrooke, M. R. et al Nature (1984) - submitted). In some cells, such as those found in medullary thyroid carcinoma and lung carcinoma, human CGRP is produced in varying levels. The presence of human CGRP may therefore be diagnostic of abnormal tissue. We further provide therefore diagnostic reagents (with antibodies and gene probes) for use in the assay of human CGRP gene expression and abnormal gene organisation.

In an eleventh aspect of the invention we provide a peptide of the structure I, or a portion thereof including an antigenic determinant, wherein the peptide or the portion thereof has a detectable label attached thereto. The label may be an enzyme, a chromophore, a fluorophore or a chemiluminescent group. Most preferably however the label is a radiactive isotope, for example $^{125}$I attached to the histidine amino acid residue at position 10 in the amino acid sequence of the peptide. Preferably the labelled peptide comprises the peptide of structure I or a portion thereof which further includes a tyrosine amino acid residue optionally labelled with $^{125}$I. Preferably the portions of the peptide are from amino acid 25 to 37 inclusive (amidated phenylalamine) or from amino acid 1 to 8 inclusive.

In a twelth aspect of the invention we provide an antibody having specificity for an antigenic determinant of the peptide of structure I. The antibody may be a polyclonal or monoclonal antibody. The antibody may be labelled with a detectable label.

The reagents of the eleventh and twelfth aspects of the invention allow for the immunoassay, preferably the radioimmunoassay, for the peptide of structure I in a sample, or for the immunocyto chemical localisation in tissue sections.

It is also possible to assay for mRNA coding for PAF-37 or the nucleotide sequence including such mRNA.

In an eleventh aspect of the invention therefore we provide a DNA hybridisation probe comprising a sequence of 15 or more nucleotides selected from the nucleotide sequence from 1 to 1256 as shown in FIG. 2 of the accompanying drawings. The probe may be immobilised on a solid phase, capable of immobilisation on a solid phase or may be labelled with a detectable label.

Such probes may be used to examine gene organisation or gene expression by DNA or RNA blotting techniques or to identify by in situ hybridisation cells in tissue sections expressing the gene.

A preferred probe of the thirteenth aspect of the invention comprises a sequence selected from the nucleotide sequence from 1 to 725 inclusive as shown in FIG. 2. A probe of this preferred type may be used to examine human CGRP as opposed to human calcitonin gene organisation or expression. In particular the probe will hybridise to human CGRP mRNA and to the human CGRP structural genes.

An alternative preferred probe of the thirteenth aspect of the invention comprises a sequence selected from the nucleotide sequence from 726 to 1256 inclusive as shown in FIG. 2. A probe of this preferred type may be used to examine the organisation of the human calcitonin CGRP gene. In particular, the probe will hybridise to an intron region of the human CGRP structural gene.

Figure 3:
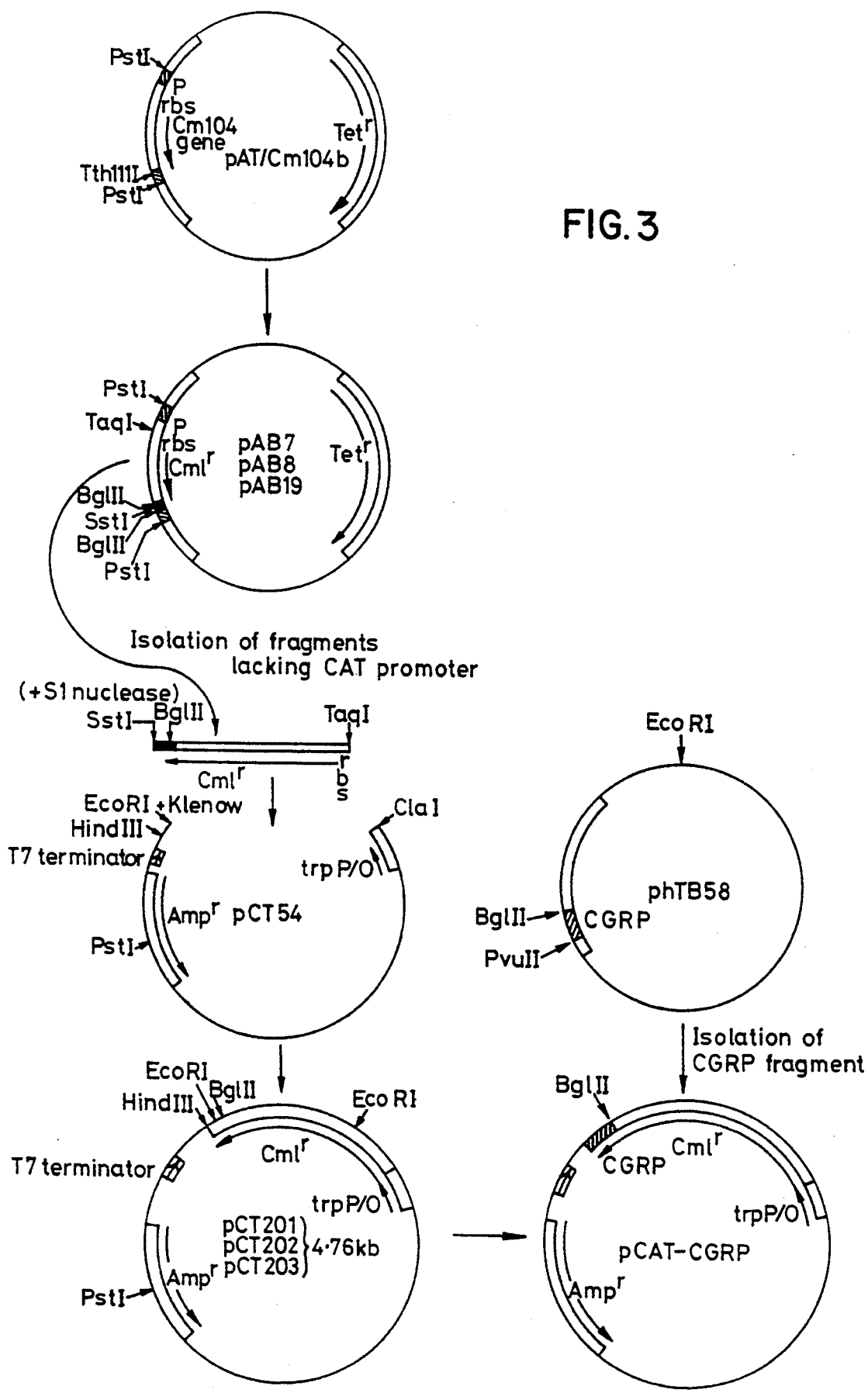
Figure 5:
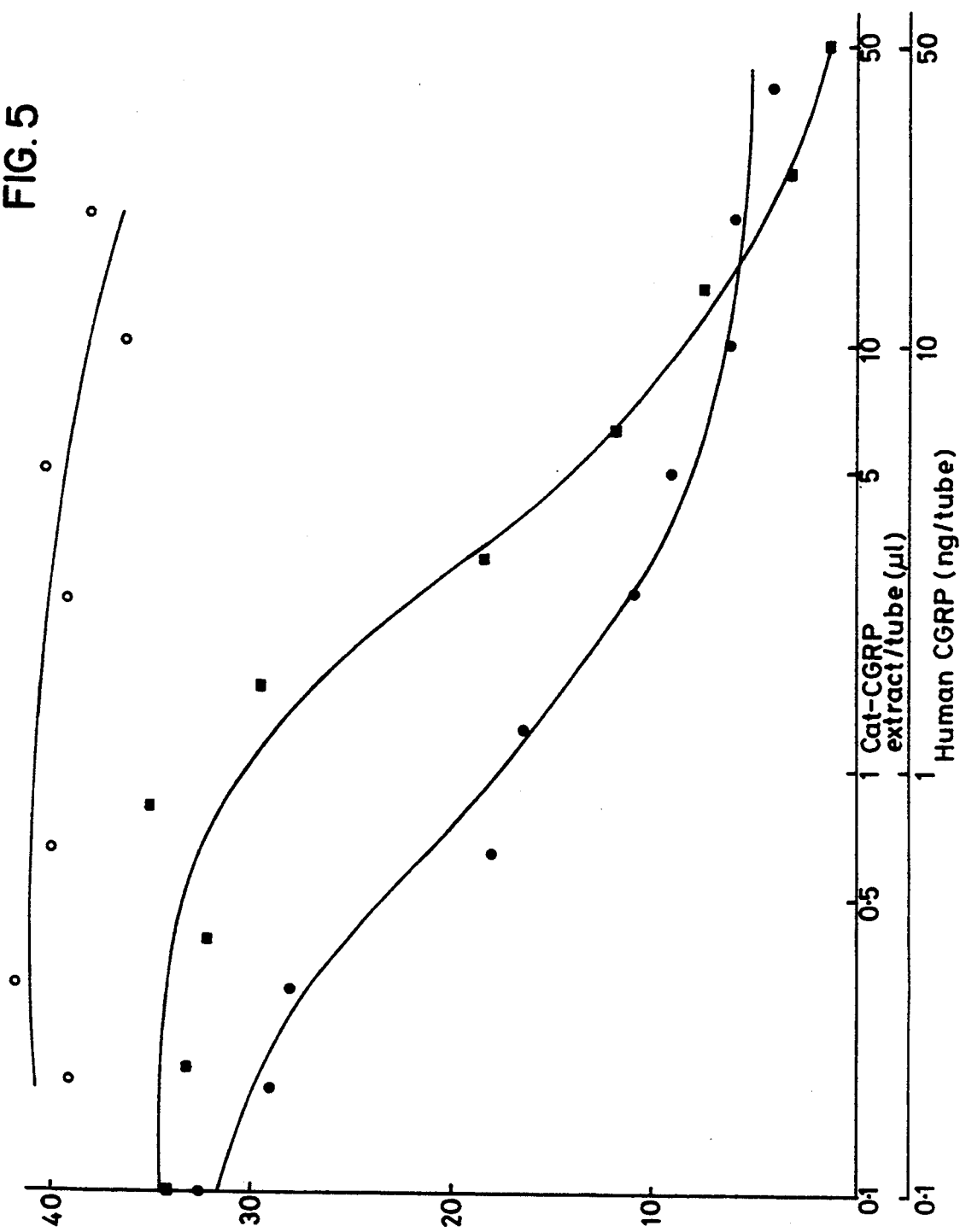
Figure 6A:
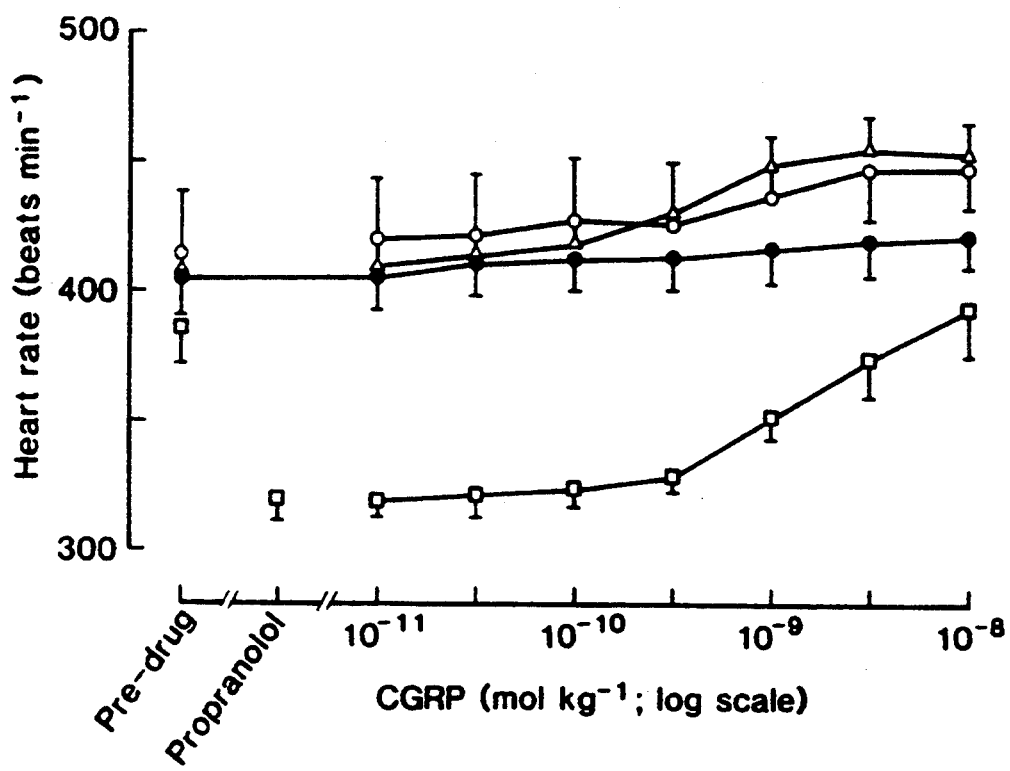
Figure 6B:
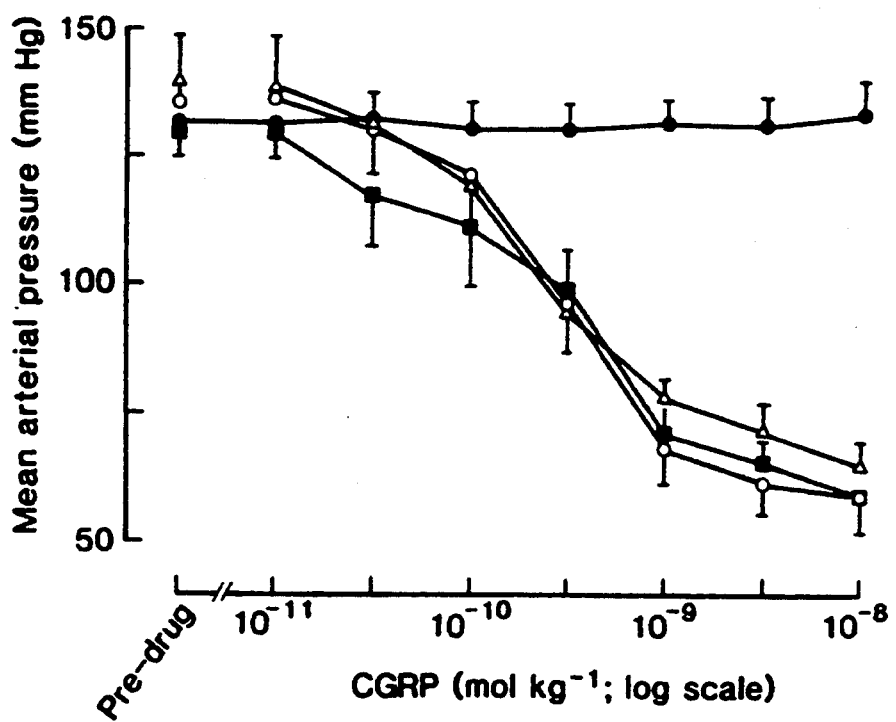

The invention is now illustrated by the following description with reference to the accompanying drawings in which:

FIG. 1 - is a schematic representation of overlapping cDNA sequences cloned within recombinant plasmids phTB3, phTB6 and phTB58, FIG. S2A to 2F - are the complete nucleotide sequence derived from recombinant plasmids phTB3, phTB6 and phTB58, FIG. 3 - is a schematic representation of the construction of plasmids pCT201, pCT202, pCT203, and pCAT-CGRP, FIGS. 4A and 4B - are a polyacrylamide gel showing the presence of a fusion protein of chloramphenicol acetyltransferase (CAT) and human CGRP in an extract of E.coli HB101 transformed with vector pCAT-CGRP, FIG. 5 - shows a graph which demonstrates the results of a radioimmunoassay revealing the presence of human CGRP antigenic determinants in a protein extract of E. coli. HB101 transformed with pCAT-CGRP, FIGS. 6A and 6B - show dose response curves for heart rate and mean arterial pressures in rats ●=saline; O=Human CGRP; △=Rat CGRP; □=Human CGRP+Propranolol; ■=Human CGRP+mepyramine+Cimetidine)

Figure 7A:
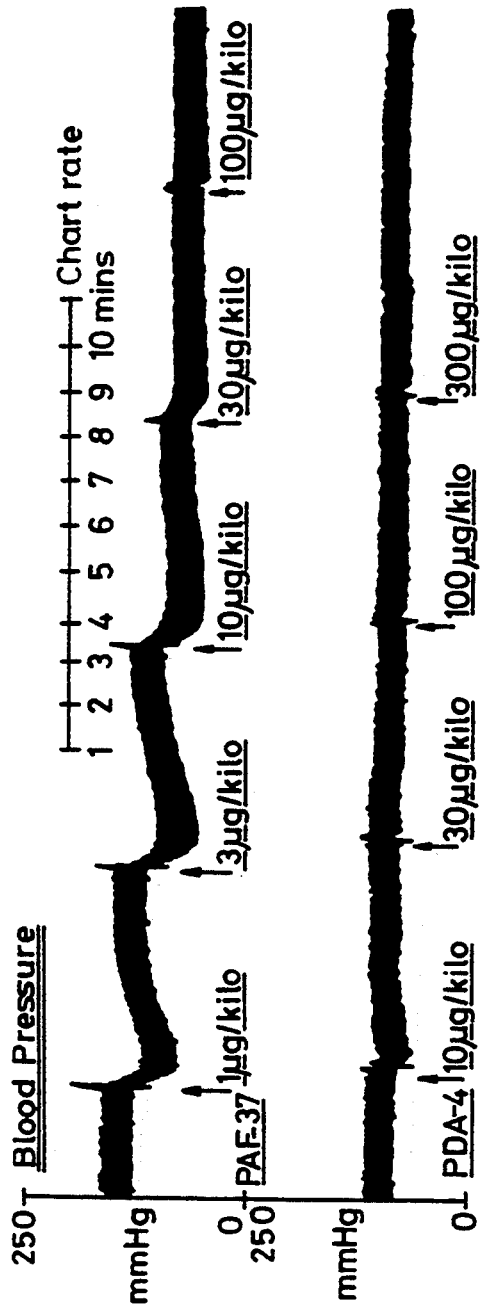
Figure 7B:
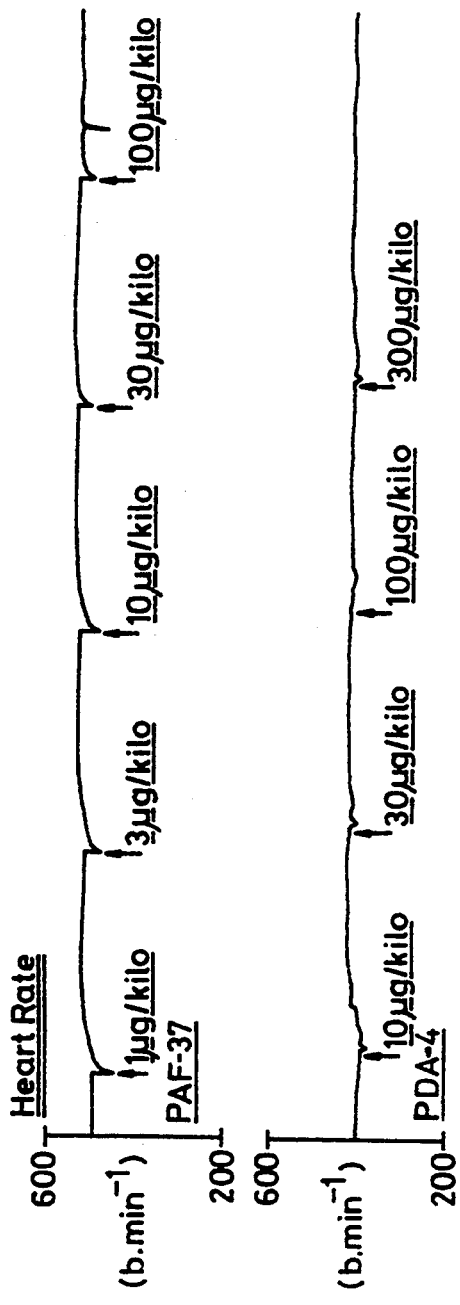

FIGS. 7A and 7B - show a tachograph trace demonstrating the effect on heart rate and mean arterial pressure of PDA-4 (and human CGRP) injected i.v. in rats.

Figure 8A:
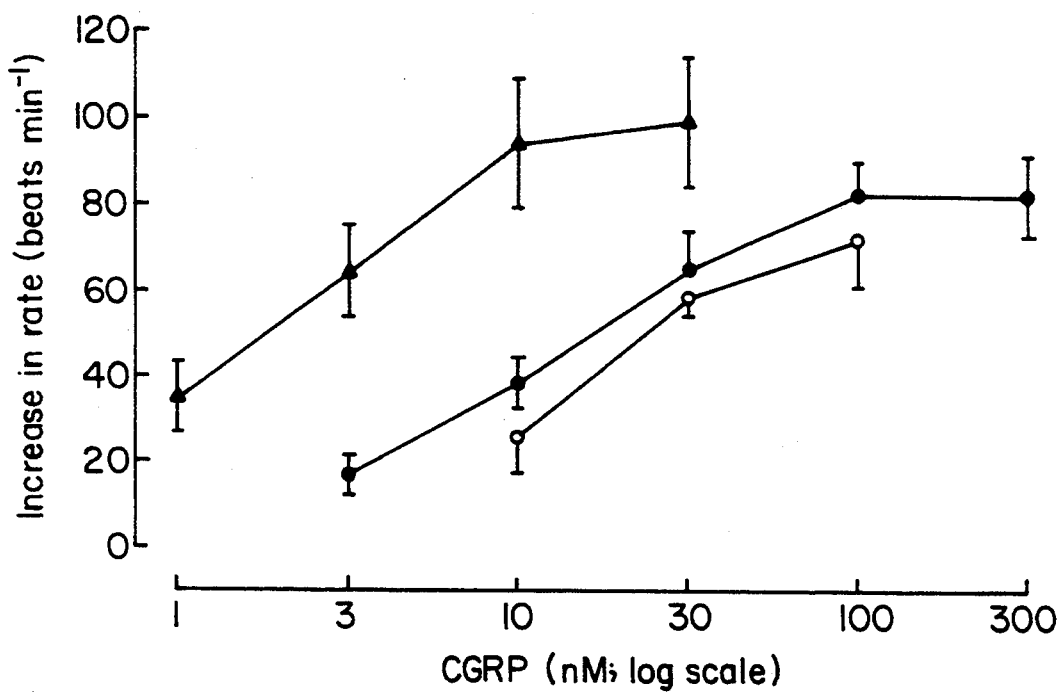
Figure 8B:
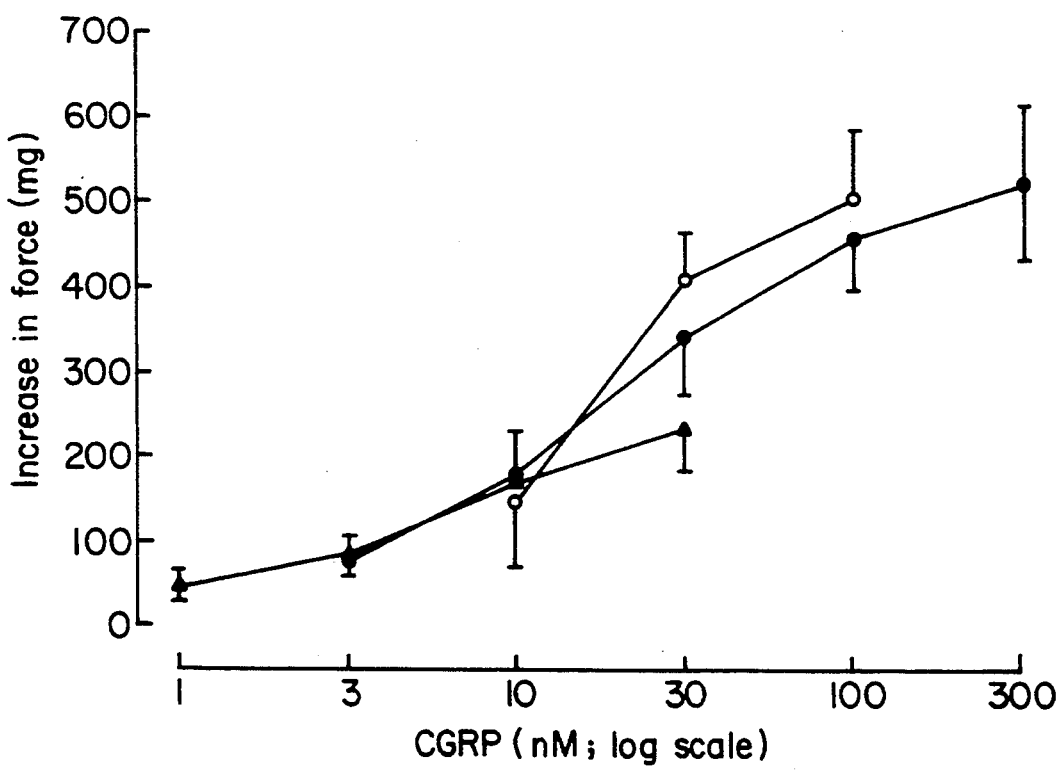

FIGS. 8A and 8B - show dose response curves for heart rate and beat force in guinea pigs ●=Human CGRP; △=Rat CGRP; O=Human CGRP+Propranolol)

Figure 9:
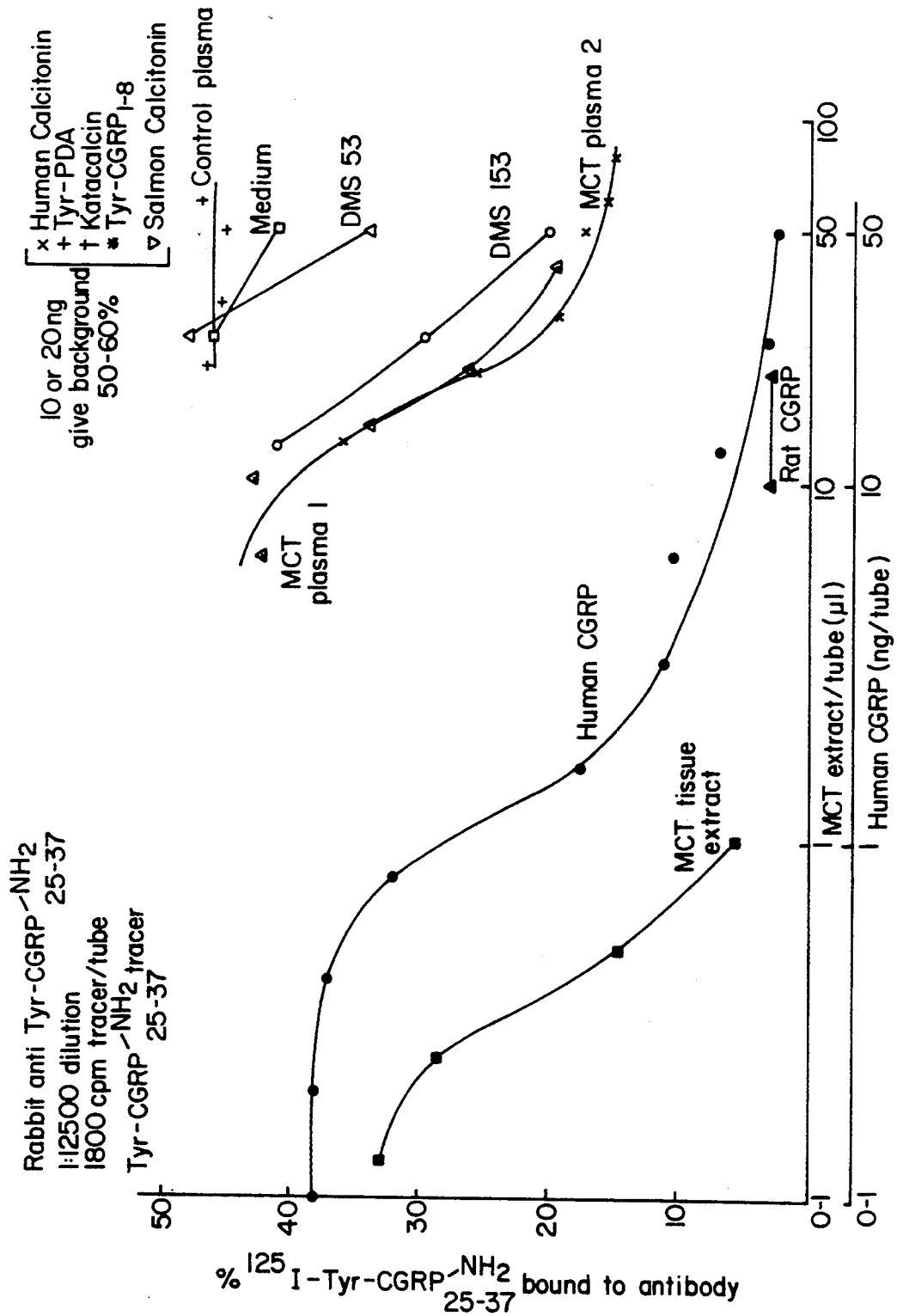

FIG. 9 - shows a graph which demonstrates the results of a radiommunoassay which reveals the presence of human CGRP in extracts of medullary thyroid carcinoma tissue, plasma from patients with medullary thyroid carcinoma and the production of CGRP by lung carcinoma cell lines.

Figure 10C:
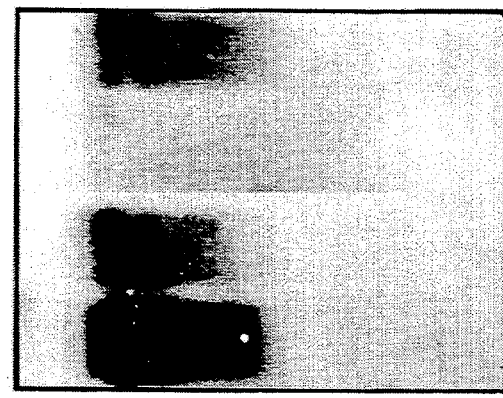
Figure 10B:
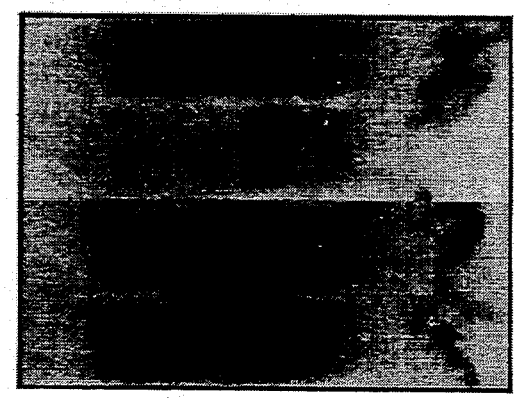
Figure 10A:
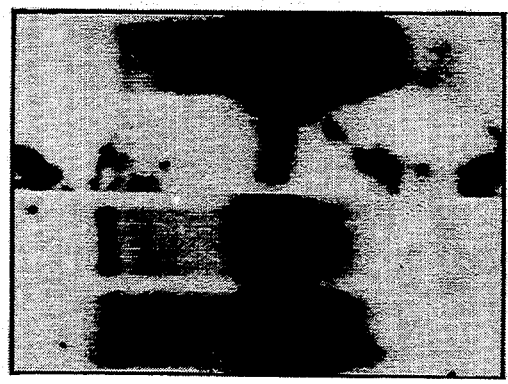
Figure 11:
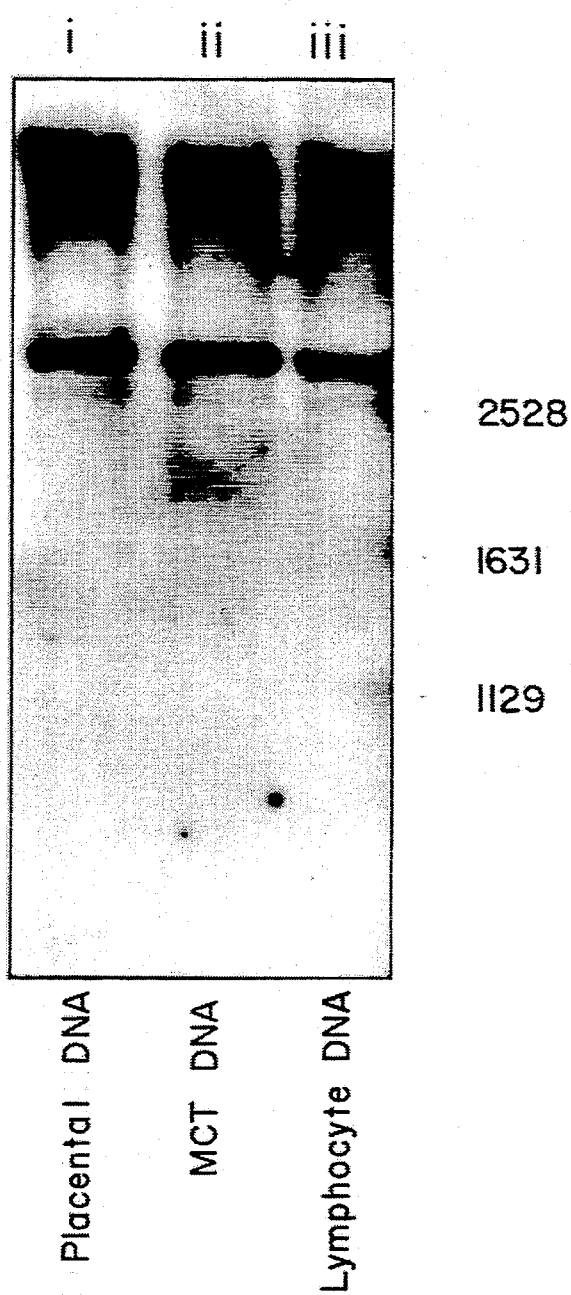

FIGS. 10A, 10B, and 10C - show an RNA blot which demonstrates the differential expression of calcitonin and human CGRP RNA in medullary thyroid carcinoma and lung carcinoma cell-lines, FIG. 11 - shows a DNA blot which demonstrates the differential organisation of the human CGRP gene and homologous genes when comparing DNA from human placental tissue with DNA from medullary thyroid carcinoma tissue or lymphocytes from a single patient.

In our copending European published application EP-A1-0070675 there is described the construction of a cDNA library using total cellular poly(A)-containing RNA isolated from human medullary thyroid carcinoma tissue (see also Allison J. et al Biochem J. (1981) 199 p 725–731) and the nucleotide sequence analysis of the greater part of the human calcitonin mRNA cloned within two plasmids isolated from this library, phT-B3 and phT-B6 (see also Craig, R. K. et al Nature (1982) 295 p 345–347). During this study, one recombinant plasmid phT-B58 containing an inserted cDNA fragment of about 1600 bp was identified during preliminary screening but not analysed further since it appeared too large to represent the calcitonin mRNA. Subsequent restriction enzyme analysis of the cDNA inserted in this plasmid (see FIG. 1) showed sites in common with phTB3 and moreover indicated that the cDNA cloned within phT-B58 represented sequence downstream from sequence previously established to represent the complete 3' untranslated region of the human calcitonin mRNA. FIG. 1 shows restriction sites separating regions of sequence subsequently used as sequence specific hybridisation probes and the relative positions of calcitonin, CGRP and the common amino terminal peptide. Vertical broken lines denote Pst I sites separating cDNA and plasmid sequences. Nucleotide sequence analysis of the entire cDNA sequence inserted into phT-B58 was performed using the method previously described (Craig, R. K., Hall, L., Edbrooke, M. R., Allison, J. & MacIntyre, I. (1982) Nature, 295, 345–347) - see FIG. 2. The figure compares known nucleotide sequence of human and rat calcitonin and CGRP RNA transcripts with gaps introduced to maximise homologies. Numbers immediately above the human nucleotide sequence denote the relative number of nucleotides from the poly(A)tail cloned into phTB58. Numbers above the human protein sequence refer to amino acid position relative to calcitonin or CGRP. Alternative or additional amino acids or nucleotides present within rat relative to human sequence are shown immediately below the codons in question. Potential polyadenylation signals are underlined. A thin arrow indicates the 3' end of the mature calcitonin mRNA, whilst heavy arrows (▲) indicate the probable position of additional introns in the human genomic sequence. Broken lines show regions of human sequence absent from the rat calcitonin gene. The inserted cDNA sequence contained 1615 bp, terminating with a tract of poly(A) residues at the 3' terminus. Of these, the first 356 bp from the 5' end were identical to those previously described, and represented part of the human calcitonin mRNA encoding Katacalcin and the whole of the 3' untranslated region including the AATAAA box and 12 nucleotides previously shown to precede the poly(A) tail in the mature calcitonin mRNA. Analysis of the remaining sequence showed it to contain a single open reading frame encoding 53 amino acids followed by a termination codon. This was preceded immediately on the 5' side by a splice junction acceptor site $(C)_n$ NAG/G (Mount, S. M. Nucleic Acid. Res. (1982) 10 p 450–463) and a further 645 nucleotides of 'intron'-like sequence separated from previously known calcitonin mRNA sequence by three adenosine residues. However no recognisable donor splice junction was present between the intron-like sequence and sequence known to be present in the human calcitonin mRNA. The novel open reading frame was followed by a tract of 451 nucleotides containing two polyadenylation signals, the first (AATAA) 26 bases downstream of the termination codon, and the second (AAAATTAAAAA) positioned 18 nucleotides before the terminating poly(A) tract. The coding sequence comprised human CGRP (a peptide of 37 amino acids) flanked at the amino terminal end by paired basic amino acids ($-1$, $-2$) and a further five amino acids ($-3$ to $-7$), and at the carboxyl end by a glycerine residue ($+1$) four basic amino acids ($+2$ to $+5$) and a tetrapeptide ($+6$ to $+9$). The presence of the glycerine reflects the requirement in vivo for an amidated carboxyl terminal phenylalanine (see Bradbury, A. F. et al nature (1982) 298 p 686–688) resulting in a calculated Mr of 3786 for the amidated human CGRP. Comparison of the predicted human amino acid sequence with that of the rat (Amara et al Nature (1982) 298 p 240–244) shows sequence conservation, with seven amino acid changes out of the 53 amino acids, four within the human CGRP (alanine 1; aspartic acid 3; asparagine 25; lysine 35), the remaining three ($-7$, $-6$, $-5$) residing in the 5 amino acid amino terminal leader sequence. Of the latter, the first amino acid (arginine $-7$) we have assigned on the basis of the position of the splice junction and by analogy with the rat calcitonin gene. Significant sequence conservation is apparent at the nucleotide level within the coding region, but is markedly reduced in the 3' non-coding region on comparison of the human sequence with available rat CGRP mRNA sequence. Comparison of the human CGRP amino acid sequence with other protein sequences (Wilbur, N. J. et al PNAS (1983) 80, p 726–730) revealed (rat CGRP apart) no significant homology with other known peptides including the calcitonins. At best nine matched amino acids were identified by alignment of human CGRP with salmon calcitonin.

Using isolated cDNA fragments from phT-B3 and phT-B58 we have established by Southern Blotting of restricted human genomic DNA that the cDNA cloned into phT-B58 represents a partially processed polyadenylated RNA transcript. In addition to the 'intron' identified by nucleotide sequence analysis, an intron has been mapped to the 3' side of the CGRP coding sequence, and others to the 5' side of the calcitonin coding sequence suggesting a genomic organisation very similar to that of the rat calcitonin gene (Rosenfeld, M. G., Mermod, J—J., Amara, S. G., Swanson, L. W., Sawchenko, P. E., Rivier, J., Vale, W. W. & Evans, R. M. (1983) Nature, 304, 129–135). However, the 'intron' like sequence separating the calcitonin exon and CGRP coding sequence truly represents the genomic organisation, since a 1125 by SphI/PvuII DNA fragment which includes calcitonin, intron and CGRP sequence isolated from phT-B58 (see FIG. 1) electrophoreses with a genomic fragment of identical size after Southern Blot analysis of human placental DNA restricted with SphI/PvuII as determined by hybridisation to an 'intron' specific hybridisation probe.

Production of human CGRP by recombinant DNA techniques

In order to produce human CGRP by a recombinant DNA technique, vectors capable of producing a fusion protein comprising an active portion of a chloramphenicol acetyltransferase protein (CAT) and a desired intermediate peptide were produced. (The vectors are described generally in copending International patent application PCT/GB 84/00179 and in British patent application 8413301 filed May 24, 1984).

A plasmid had been isolated by Pst1 digestion of the DNA of a weakly chloramphenicol resistant R100 R-plasmid mutant and subsequent ligation of a single Pst1 fragment into the Pst1 site of plasmid pBR322 (Iida et al (1982) EMBO J. 1, 755–759). The plasmid, pBR322: Cm104, was obtained and encodes a $CAT_I$ enzyme that has had the last seven amino acid residues of the carboxy terminus removed by deletion. The removal was due to a spontaneous in vivo mutation which involved the insertion element IS1. However, the resulting DNA molecule has no termination codon at the end of the $CAT_I$ structural gene. The ribosome, therefore, translates into protein the RNA transcribed from the IS1 DNA until it meets an in phase termination codon. The net result is a $CAT_I$ protein nineteen amino acid residues longer than the native enzyme in which the last twenty-six amino acid residues are directed by the IS1 DNA sequence. This structural gene also lacks any suitable restriction sites which would be useful to create a desirable fusion protein so a series of DNA manipulations were performed.

A Pst1 restriction fragment containing the mutant $CAT_I$ gene outlined above was isolated from plasmid pBR322: Cm104 and ligated into the dephosphorylated Pst1 site of plasmid pAT153. The plasmid pAT/Cm104b (FIG. 3) was chosen since in this orientation both the $CAT_I$ and β-lactamase promoters transcribe in the same direction. This cloning maneouvre was primarily to construct a plasmid which carries a unique Tth111I restriction site. This cleavage site is derived from the IS1 DNA which was joined to the end of the $CAT_I$ structural gene and lies in the nineteenth amino acid codon of the twenty-six amino acid residue extension described above.

Plasmid pAT/Cm104b was linearised with Tth111I and digested with BAL31 exonuclease. Samples at a series of time points were withdrawn and the reaction was stopped using excess EDTA. Any non-flush ends created by the BAL31 digestion were filled in using the Klenow fragment of DNA polymerase I. These plasmid DNA molecules were then dephosphorylated using calf intestinal phosphatase. Next a kinased linker, R140 with the sequence

5'-TCAGATCTGGAGCTCCAGATCTGA-3' was ligated to each plasmid time point sample. After ligation the plasmid DNAs were digested with SstI restriction endonuclease and re-ligated to ensure that only one linker was present in each plasmid.

These sets of DNA molecules were then transformed into E. coli DH1 and fusion vector plasmids were selected on the basis of vigorous growth on L-agar containing 20 μg/ml chloramphenicol.

Small scale plasmid preparations were performed. A number of plasmids which carried a single Sst1 restriction site (derived from the linker DNA) and which also generated a comparatively small DNA fragment when simultaneously digested with EcoR1 and BglII were isolated. DNA sequence analysis revealed that in plasmid pAB7, pAB8 and pAB19 the linker DNA had been attached to the 3' end of the $CAT_I$ structural gene in each of the three reading frames.

Plasmids pAB7, pAB8 and pAB19 were each digested with restriction enzyme SstI and incubated with S1 exonuclease. After phenol/chloroform extraction and ethanol precipitation these blunt-ended plasmid molecules were digested with TaqI and DNA fragments of approximately 750 base pairs were isolated. These fragments contain the entire $CAT_I$ fusion structural genes with BglII sites in three reading frames but lack the $CAT_I$ promoter.

These $CAT_I$ genes were then put under the control of the trp promoter of plasmid pCT54 (Emtage et al, Proc Natl Acad Sci USA 80, 3671-3675, 1983). This plasmid also has the advantage of having a transcription terminator sequence so that high level expression is limited to the gene cloned upstream of this sequence and downstream of the trp promoter. Plasmid pCT54 was digested with EcoR1 and the 5' cohesive ends were filled in using the Klenow fragment of DNA polymerase I. Subsequent restrictions of this molecule with the enzyme Cla1 followed by dephosphorylation created a molecule which would accept the $CAT_I$ fusion vector gene cartridges isolated above. Ligation of this molecule with a 3-fold molar excess of each the $CAT_I$ gene cartridges followed by transformation of E coli HB101 gave the chloramphenicol resistant fusion vector plasmids pCT201, pCT202 and pCT203 (FIG. 3). (NB in all three cases the manipulation result in the reformation of the EcoR1 site of pCT54).

The plasmid vector pCT 203 was cut with Hind III. This gave plasmid DNA having Hind III sticky ends which were then blunted with DNA polymerase. The resultant plasmid DNA was then further cut with Bg1 II to yield DNA molecules having a Bg1 II sticky end and a blunt end. The resultant DNA was then ligated with the Bg1 II-Pvu II fragment of plasmid phT-B58 (see FIGS. 1 and 3) to give circular plasmid molecules. These plasmid molecules were then transformed into E. coli HB101 cells and E. coli HB101/pCAT-CGRP transformants were selected by growth on medium containing ampicillin (100 ug/ml). On culturing, the E. coli HB101/pCAT-CGRP cells produced a fusion protein having the predicted size, as judged by SDS polyacrylamide gel electrophoresis and Commassie Blue staining (FIG. 4a), or by SDS polyacrylamide gel electrophoresis followed by autoradiography (FIG. 4b) after pulsing cells for 1 min. with $^{35}S$ methionine (see Emtage, J. S. et al PNAS (1983) 80, p 3671-3675). Thus in the pCAT-CGRP constructs a novel protein is produced see - Fig. 4(a), 4(b) Lanes 1,2) compared with the CAT protein alone - FIG. 4(a),4(b) Lane 3. Lane M shows molecular weight marker proteins and their respective molecular weights.

Evidence that the fusion protein produced, contains CGRP protein sequence was determined by radioimmunoassay of HB101/pCAT-CGRP cell extracts. Cells from a 500 ml culture were harvested and lysed in a lysozyme/sodium deoxycholate mixture (5 ml), then treated with DNase for 30 mins. at 5° C. (Emtage J. S. et al PNAS (1983), 80, p 3671-3675). An equal volume of 0.1M Tris HCl pH 8.0, 0.1 mM EDTA, 5% (v/v) glycol, was then added, and the presence of human CGRP sequence determined in the extract. Radioimmunoassay was carried out in 0.05M phosphate buffer pH 7.4 in a final volume of 400 ul (see Girgis, S. I. et al J. Endocrinol 78, 372-382). Antiserum was raised in rabbits, using the known techniques, against Tyr-(CGRP amino acids 25-37)-amide and conjugated to chick ovalbumin (Reichlin, M.1980, Meth.Enzymol 70 159-165) and against $^{125}I$ Tyr-(CGRP amino acids 25-37)-amide tracer.

The tracer was iodinated using the Chloramine T method of Hunter and Greenwood. It can be seen from FIG. 5 that HB101/pCAT-CGRP protein extract displaced the tracer (5000 cpm) using a 1:10000 serum dilution with a displacement curve similar to that of the human CGRP standard (chemically synthesised). No displacement was observed using protein extract which had been previously digested overnight with trypsin (0.5 mg/ml) overnight at 37° C. followed by inactivation of the trypsin with trasylol. Goat anti rabbit serum was used to quantitatively precipitate rabbit IgG and bound $^{125}I$ tracer after the addition of 1 ul of preimmune rabbit sera as a carrier (Craig R. K. et al (1976 Biochem J. 160 p 57-74 and the precipitated $^{125}I$ quantitated by γ-counting. This demonstrates the production of human CGRP peptide sequence by HB101/pCAT-CGRP.

The construction of the pCAT-CGRP plasmid was checked by ScaI digestion - this gave a DNA band on a gel that was bigger by the predicted amount, than the corresponding band obtained from pCT203. The plasmid construction was also checked by HaeII digestion. The BglII-Pvu II cDNA fragment from phT-B58 contains an HaeII site that is not present in pCT203 and the gels showed a cDNA band of the expected size.

The fusion protein produced by pCAT-CGRP comprises the amino acid sequence of CGRP with additional amino acid residues at the carboxyl terminal and the amino terminal (see FIG. 1). The amino terminal includes the sequence Lys-Arg immediately preceding CGRP. This provides a site for clostripain cleavage, although case must be taken in view of potential clostripain sites within the CGRP. Other unique cleavage sites may be used.

Production of human CGRP by chemical synthesis

Human CGRP in its amidated form fragments or analogues thereof, and PDA-4 were synthesised by Celltech Limited 244-250 Bath Road, Slough, Berkshire SL1 4D7, United Kingdom or by Peninsula Laboratories Inc., 61 Taylor Way, Belmont, Calif. 94002 U.S.A. The standard techniques of peptide synthesis may be used - for example the Merrifield solid phase peptide synthesis or the so - called FMOC procedure (see "Solid Phase Peptide Synthesis - A Reassessment" by R. C. Sheppard - from Molecular Endocrinology eds. MacIntyre and Szelke, Elsevier (1977) P 43-56; E. Atherton et al J. C. S. Chem. Comm (1981) p 1151-1152; and G. Barany and R. B. Merrified in "The Peptides" eds E. Gross and J. Jeienhofer, Academic Press, New York (1980) p 3.

Cardiovascular actions of human CGRP

Using the amino acid sequence predicted by nucleotide sequence analysis of phT-B58, amidated human CGRP has been chemically synthesised and then purified using a combination of ion and reverse phase chromatography. The final human CGRP preparation was pure as judged by mass spectrometry where a single ion was observed (Mr 3786). We have compared the cardiovascular effects of this preparation with a synthetic rat CGRP preparation of similar purity.

Groups of 4 to 6 male Sprague-Dawley rats (285-315 g) were anaesthetised with sodium pentobarbitone (60 mg $Kg^{-1}$ i.p.). The trachea, left carotid artery and left jugular vein were cannulated. Blood pressure was recorded from the carotid artery on a Grass polygraph via a Statham P23 ID pressure transducer and mean arterial pressure derived from the trace. Heart rate was measured by a tachograph (Grass model 7P4) triggered by the blood pressure signal. Human CGRP was obtained either crude off the resin, then purified, or latterly in a purified form from Peninsula Laboratories. Purified rat CGRP was from the same source. All synthetic preparations were subject to mass spectrometry (M-Scan Ltd.) to confirm structure and purity before use. Human CGRP, rat CGRP, propranolol hydrochloride (Sigma), mepyramine maleate (Sigma), cimetidine hydrochloride (SK & F), histamine diphosphate (Sigma) were dissolved in 0.9% w/v saline. All compounds were administered intravenously except for mepyramine (s.c.). Saline ( ), human CGRP (o) and rat CGRP (Δ) were administered cumulatively in volumes of 0.1 ml per rat at 2 min intervals. The peak fall in mean arterial pressure (MAP) and heart rate (HR) after 2 min was measured. Saline administration did not alter MAP or HR, and both human CGRP and rat CGRP evoked a dose-dependent fall in MAP and an increase in HR. Propranolol, 3.4 μmol Kg$^{-1}$ (□), 5 min before human CGRP did not prevent the increase in heart rate. Mepyramine (12.4 μmol Kg$^{-1}$) and cimetidine (59.5 μmol Kg$^{-1}$, as an infusion over 30 min) (■) significantly reduced the hypotensive response to histamine ($10^{-8}$–$10^{-5}$ mol Kg$^{-1}$) but did not significantly alter the hypotensive effect of human CGRP. Seven injections of saline over the duration of the experiment did not significantly alter either MAP or HR in the presence of propranolol or mepyramine and cimetidine.

In the pentobarbitone anaesthetised rat, intravenous human CGRP evoked a rapid dose-related fall in blood pressure, maximal within 1 min, and representing a 50% decrease in blood pressure at a dose of 0.28 nmol Kg$^{-1}$. This was not significantly different (p 0.05; t-test) from results obtained with rat CGRP(0.23 nmol. Kg$^{-1}$) FIG. 5. The hypotension was associated with small but significant increases in heart rate. Since a fall in blood pressure may be evoked indirectly by basic peptides through the release of histamine (Goth, A. (1973) In Histamine and antihistamines (Ed. Schachter, M.) Vol. I. Int. Encyclopedia of Pharmacology and Therapeutics, Section 74, 25–43 Pergamon Press, Oxford), and human CGRP is a relatively basic peptide, we have examined the effect of pretreatment with the histamine H$_1$-receptor antagonist mepyramine and the histamine H$_2$-receptor antagonist cimetidine prior to human CGRP administration. Neither antagonist had a significant effect on the hypotensive response to human CGRP (FIG. 6) or the associated tachycardia (data not shown). It has also been suggested that rat CGRP may increase heart rate through increased sympathetic drive (Fisher, L. A., Kikkawa, D. O., Rivier, J. E., Amara, S. G., Evans, R. M., Rosenfeld, M. G., Vale, W. W. & Brown, M. R. (1983) Nature, 305, 534–536). We have investigated this possibility by i.v. administration of human CGRP after pretreatment with the β-adrenoceptor antagonist propranolol (in a dose sufficient to shift an isoprenaline dose-response curve to the right by 2 log units). Following propranolol the basal heart rate was significantly reduced but human CGRP continued to evoke a tachycardia, and furthermore the threshold dose for this effect remained unchanged, compared with saline treated controls (FIG. 6). From these results we conclude that the fall in blood pressure and increase in heart rate evoked by human CGRP are not mediated indirectly via the release of either histamine or catecholamines. The duration of the response to human CGRP was measured following administration of a single dose. Human CGRP 1 nmol. Kg$^{-1}$ lowered arterial pressure from 125.0±7.6 mm Hg to 68.3±9.3 mm Hg and the time taken for the blood pressure to recover by 50% was 3.8±0.5 min.

Examination of the cardiovascular action of i.v. PDA-4 in phenobarbitone anaesthetised rats as described above showed a small but significant effect. As can be seen in FIG. 7 PDA-4 was 50-100 fold less potent than human CGRP. Thus 1 ug/kilo human CGRP resulted in an immediate 50 mmHg drop in mean arterial pressure and an increase in heart beat rate of 25-30 b.p.m. Whilst 10 ug/kilo PDA-4 caused a drop in mean arterial pressure of 15-20 mm Hg and an increase in heart beat rate of 15-20 bpm. The mechanism of action of PDA-4 was not examined.

The cardiac effects of human CGRP were also studied in vitro in order to eliminate the possible influence of reflex or other factors resulting from the fall in blood pressure in vivo.

Male Dunkin Hartley guinea-pigs (280–400 g) were killed by cervical dislocation and exsanguinated. The heart was removed, the right atrium dissected out and mounted under 0.5 g tension in Krebs solution (mM): NaCl 118, KCl 4.7, CaCl$_2$ 2.5, KH$_2$PO$_4$ 1.18, NaHCO$_3$ 25, MgSO$_4$ 1.18 and glucose 11.1, at 34° C. bubbled with 95:5 O$_2$:CO$_2$. Atrial force and rate were measured isometrically by a Grass FT.03 transducer and recorded on a Grass polygraph. Single doses of either human (●) or rat (▲) CGRP were given in a random order. Preliminary experiments showed that two consecutive dose-response curves to CGRP gave reproduceable results.

Propranolol (o) (300 nM) or cimetidine (100 μM), equilibrated for 30 min, antagonised the effects of isoprenaline (3–30 nM) or histamine (500 nM) respectively in the same experiments where these antagonists did not significantly reduce the increased rate and force evoked by CGRP. The antagonists alone did not significantly alter the basal rate (187±9 b.min$^{-1}$) or force (264±34 mg) of the isolated atria.

In the guinea-pig right atrial preparation, human CGRP evoked concentration dependent increases in the rate and force of contraction (FIG. 8). In agreement with results obtained in vivo, effective β-adrenoceptor blocking concentrations or propranolol or of the histamine H$_2$-receptor antagonist cimetidine did not alter the responses to human CGRP. Interestingly, although rat CGRP was equipotent with human CGRP in evoking increases in force, it was approximately 10 times more potent at increasing rate (FIG. 8). Neither the increase in rate or force produced by rat CGRP was blocked by propranolol. Thus rat and human CGRP appear to act directly on the isolated atria, and their actions are independent of catecholamine and histamine receptor mechanisms.

Our studies demonstrate that the peripheral cardiovascular effects of human and rat CGRP in the anaesthetised rat are similar to those reported for peripherally administered rat CGRP in conscious animals, though rat CGRP evoked a greater increase in heart rate in the conscious preparation possibly due to the blunting of cardiovascular reflexes by anaesthesia in our experiments (Morrison, J. L. Walker, H. A. & Richardson, A. P. (1950) Arch. Int. Pharmacodyn. 82, 53–62). Studies with antagonists demonstrate that the vasodepressor effect of CGRP is not mediated via histamine or catecholamines. Therefore CGRP may act on the cardiovascular system directly via a novel receptor mechanism and not through the release of other mediators. Similarly the activity of CGRP on isolated atria which was unaffected by propranolol and cimetidine supports the concept of a CGRP receptor mechanism in cardiac tissue in addition to the vasculature. The similar potency of human and rat CGRP at lowering blood pressure in vivo and increasing the force of contraction of the atria in vitro contrasts with their differing potency at increasing the rate of contraction of the atria. The results obtained in vitro suggest that rat CGRP has a preferential chronotropic (compared with inotropic) effect, a property which was not evident in vivo, possibly due to the different species employed or to the presence of the anaesthetic. We also demonstrate that PDA-4 when administered i.v. has a hypotensive effect with parallel tachycardia.

Diagnostic applications

Using the amino acid sequence predicted for human CGRP in FIG. 2, we have raised antibodies in rabbits against amidated CGRP, and also the tyrosinated analogue; Tyr-(CGRP-amino acids 25–37)-amide conjugated to ovalbumin (Reichlin, M. (1980), Meth. Enzym. 70 159–165). Both proved antigenic as determined by their ability to bind $^{125}$I Tyr(CGRP amino acids 25–37)-amide. We have used antibody raised against Tyr-(CGRP amino acids 25–37)-amide to set up a radioimmunoassay sensitive to lng CGRP/tube, using a 1:12500 dilution of serum and 1800 cpm $^{125}$I-Tyr-(CGRP amino acids 25–37) -amide tracer in a 400 μl assay as described above. Using this assay (FIG. 9), we demonstrate that the antibody does not cross-react with human calcitonin, tyrosinated PDA-4, katacalcin, Tyr-CGRP (amino acids 1–8) or salmon calcitonin, but that the antibody recognises antigenic determinants in rat CGRP, and shows the expected displacement curve when titred with increasing amounts of human CGRP. Using this assay we have identified the presence of human CGRP in extracts from human medullary thyroid carcinoma tissue (Bennett, H. P. et al 1978 Biochem J. 175, 1139–1141) and in tissue culture medium removed from a human small cell carcinoma cell-line (DMS 153), a cell-line derived from a liver metastasis (lung primary) at autopsy (Pettengill et al (1980) Cancer 45, 906–918) and known to produce low levels of calcitonin. Tissue culture medium alone did not react with the antiserum, whilst medium removed from DMS53 cells, a small cell carcinoma cell-line known to produce high levels of calcitonin (Sorenson et al 1981 Cancer 47 1289–1296) had only traces of humanCGRP. Parallel displacement curves were observed for MCT extract and DMS 153 medium. Normal human plasma did not contain detectable levels of CGRP within the range of the assay, whilst plasma from some MCT patients, contained measurable amounts.

We have also localised human CGRP producing cells by immunocytochemical means at the light level in a paraffin wax embedded human medullary thyroid carcinoma tissue, using immunostaining by the peroxidase-antiperoxidase method (Sternberger, L. A. 1979 Immunocytochemistry 2nd Edition, J. Wiley & Son, N. Y.), demonstrating the diagnostic application of these antibodies in the classification of human tumour pathology.

We have also demonstrated the diagnostic value of human CGRP gene probes, to investigate tissue and cell-specific calcitonin CGRP gene expression, and also to investigate CGRP gene rearrangement in tumour tissues. Total poly (A)-containing RNA was isolated, from two different medullary thyroid carcinoma tumours and from the DMS 53 and 153 cell-lines (see Allison et al (1981) Biochem. J. 199, 725–731 and Hall et al 1979 Nature 277, 54–56). The distribution of calcitonin, CGRP and intron specific transcripts (see FIG. 1) was investigated by RNA blotting involving separation by electrophoresis on 1.1% (w/v) agarose gels followed by transfer to Biodyne membranes (Taylor, J. B. et al, 1984 Biochem J. 219, 223–231). In separate experiments the membranes were probed with BglII/PstI $^{32}$P-labelled calcitonin specific cDNA fragments (Sp. Ac 3.2×10$^8$ cpm/ug), a BglII/PstI CGRP specific cDNA fragment (Sp. Ac. 7.9×10$^8$ cpm/ug), and a BglII/BglII 'intron' specific cDNA fragment (Sp. Ac. 2.8×10$^8$ cpm/ug)-see FIG. 1. The filters were washed, then autoradiographed. This demonstrated (FIG. 10), in agreement with RLA data, that calcitonin and CGRP mRNA species were expressed at different levels in the cell-lines and tumours, and that calcitonin and CGRP mRNA were probably processed from a common transcript via different processing pathways. Also that the intron specific sequence was not present in the mature processed calcitonin or CGRP mRNA species.

Investigation of genomic organisation of the human CGRP gene sequence after restriction endonuclease digestion of normal placental DNA and also MTC tissue DNA and blood lymphocyte DNA from a patient (FIG. 11) also produced differences in gene organisation. Thus 20 μg of each DNA sample was restricted with BamHI, and the fragments separated on the basis of size by electrophoresis on a 1% (w/v) agarose gel, blotted onto Gene Screen Plus membrane (NEN), then probed using a BglII/PstI CGRP specific cDNA probe labelled to a specific activity of 10$^8$ cpm/ug. Hybridisation was performed overnight in 50% (v/v) formamide, 1% (w/v) SDS, 10% (w/v) dextran sulphate in 50 mm Tris-HCl pH 7.5. Filters were then washed successively in 2×SSC at RTP; 2×SSC, 1% (w/v) SDS at 65° C. for 30 min., and 0.1×SSC at 65° C. for 15 min then autoradiographed for 48 h. This demonstrated (FIG. 11) a single major band of hybridisation (2.8 kb) and a minor band (2.6 kb) in all DNA samples, but an additional minor band (3.0 kb) in the placental DNA. Thus using a CGRP specific cDNA probe we have identified gene rearrangements, in this instance in a gene which shows homology with the probe, as opposed to being homologous. Such observations point to the diagnostic value of sequence specific probes in the investigation of gene rearrangements in tumour tissue, and in this instance the possibility of using a CGRP gene probe to investigate linked restriction enzyme polymorphisms in the familial form of medullary thyroid carcinoma.

Summary

Our studies on human calcitonin gene expression at the molecular level, and investigation of the cardiovascular activity of synthetic human CGRP corroborates and extends work by others using the rat calcitonin gene as a model system (Amara, S. G., Jonas, V., Rosenfeld, M. G., Ong, E. S. & Evans, R. M. (1982) Nature, 298, 240–244) (Rosenfeld, M. G., Mermod, J—J., Amara, S. G., Swanson, L. W., Sawchenko, P. E., Rivier, J., Vale, W. W. & Evans, R. M. (1983) Nature, 304, 129–135) (Fisher, L. A., Kikkawa, D. O., Rivier, J. E., Amara, S. G., Evans, R. M., Rosenfeld, M. G., Vale, W. W. & Brown, M. R. (1983) *Nature*, 305, 534–536). We have identified calcitonin and CGRP mRNA sequences in human thyroid and lung carcinoma, observations supported by the identification using antibodies raised against human CGRP or fragments thereof, of CGRP in lung carcinoma cell lines and in medullary thyroid carcinoma tissue and plasma. Thus measurement of plasma CGRP levels, the histological examination of tissues using in situ hybridisation or immunocytochemical techniques, or the examination of gene structure and expression, using DNA and RNA blotting may be of value in the management of medullary thyroid carcinoma (Hill, C. S., Ibanez, M. L., Samaan, N. A., Ahearn, M. J. & Clark, R. L. (1973) *Medicine*, 52, 141–171) lung carcinoma and diseases known to be associated with abnormal calcitonin gene expression for example osteoporosis.

Our observations that amidated human CGRP peptide PDA-4 have an effect on the cardiovascular system causing an increase in rate and force of contraction of the heart, and a hypotensive effect, suggests a role for the peptides in the clinical management of hypertension. Our studies also demonstrate that the peripheral action of CGRP is independent of catecholamine β-receptors and histamine receptors. In the light of the rapid onset of the hypotensive response following the peptide, the present results are consistent with the view that CGRP may act directly on the cardiovascular system through a novel receptor mechanism independent of other mediators.

We claim:

1. A 37 amino acid human calcitonin gene related peptide having the amino acid sequence of a product of the human calcitonin gene system.

2. A peptide having the structure;

Ala—Cys—Asp—Thr—Ala—Thr—Cys—Val—Thr—His—Arg—
—Leu—Ala—Gly—Leu—Leu—Ser—Arg—Ser—Gly—Gly—
—Val—Val—Lys—Asn—Asn—Phe—Val—Pro—Thr—Asn—
—Val—Gly—Ser—Lys—Ala—Phe—amide. (I)

3. A pharmaceutical composition comprising a peptide according to claim 2 and a pharmaceutically acceptable excipient.

4. A method of treatment of hypertension comprising administering to a person in need of same an effective amount of the peptide having the structure:

Ala—Cys—Asp—Thr—Ala—Thr—Cys—Val—Thr—His—Arg—Leu—Ala—Gly—Leu—
Leu—Ser—Arg—Ser—Gly—Gly—Val—Val—Lys—Asn—Asn—Phe—Val—Pro—Thr—
Asn—Val—Gly—Ser—Lys—Ala—Phe—amide.

* * * * *